(12) United States Patent
Benzel et al.

(10) Patent No.: US 6,906,392 B2
(45) Date of Patent: Jun. 14, 2005

(54) MICROMECHANICAL COMPONENT

(75) Inventors: Hubert Benzel, Pliezhausen (DE); Heribert Weber, Nuertingen (DE); Michael Bauer, Tuebingen (DE); Hans Artmann, Magstadt (DE); Thorsten Pannek, Stuttgart (DE); Frank Schaefer, Tuebingen (DE); Christian Krummel, Kirchentellinsfurt (DE)

(73) Assignee: paragon, Delbruck (DE)

( * ) Notice: Subject to any disclaimer, the term of this patent is extended or adjusted under 35 U.S.C. 154(b) by 0 days.

(21) Appl. No.: 10/381,307

(22) PCT Filed: Jul. 6, 2002

(86) PCT No.: PCT/DE02/02480

§ 371 (c)(1),
(2), (4) Date: Mar. 24, 2003

(87) PCT Pub. No.: WO03/012420

PCT Pub. Date: Feb. 13, 2003

(65) Prior Publication Data

US 2004/0021184 A1 Feb. 5, 2004

(30) Foreign Application Priority Data

Jul. 6, 2002 (DE) .............................. PCT/DE02/02480

(51) Int. Cl.[7] .............................. H01L 27/14; G01N 7/00
(52) U.S. Cl. ...................... 257/414; 257/532; 257/536; 73/31.06
(58) Field of Search ................................ 257/414, 622, 257/532, 536; 73/31.06

(56) References Cited

U.S. PATENT DOCUMENTS 5,464,966 A 11/1995 Suehle et al.
5,659,127 A 8/1997 Shie et al.
6,265,222 B1 * 7/2001 DiMeo et al. ............... 436/144
2004/0021184 A1 * 2/2004 Benzel et al. ............... 257/414

FOREIGN PATENT DOCUMENTS

| DE | 44 00 838 | 7/1995 |
| DE | 197 52 208 | 6/1999 |
| EP | 0 882 978 | 12/1998 |
| WO | WO 98 50763 | 11/1998 |

OTHER PUBLICATIONS

Maccagnani P et al; "Thick Porous Silicon Thermo–Insulating Membranes"; Sensors and Materials, Scientific Publishing Division of Myu, Tokyo, JP, pp. 131–147, 1999.

Lammal G et al.; "Free–Standing, mobile 3D porous silicon microstructures"; Sensors and Actuators A, Elsevier Sequoia S.A.; Aug. 25, 2000; pp. 356–360.

Lang et al.; "Porous Silicon Technology for Thermal Sensors"; Sensors and Materials, Scientific Publishing Division of Muy, Tokyo, JP; pp. 327–344, 1996.

* cited by examiner

Primary Examiner—Mark V. Prenty
(74) Attorney, Agent, or Firm—Kenyon & Kenyon

(57) ABSTRACT

A micromechanical component includes a substrate and a cover layer deposited on the substrate, underneath the cover layer, a region of porous material being provided which mechanically supports and thermally insulates the cover layer. On the cover layer, a heating device is provided to heat the cover layer above the region; and above the region, a detector is provided to measure an electric property of a heated medium provided above the region on the cover layer.

16 Claims, 3 Drawing Sheets

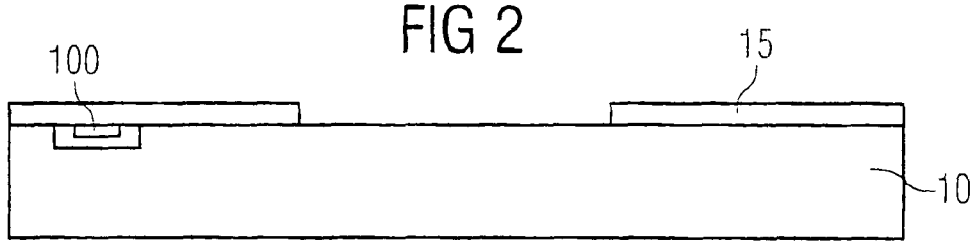
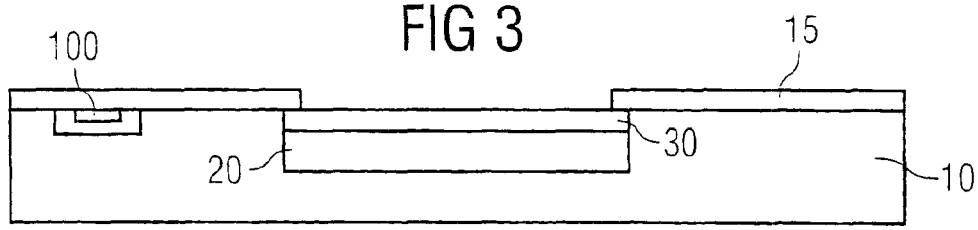
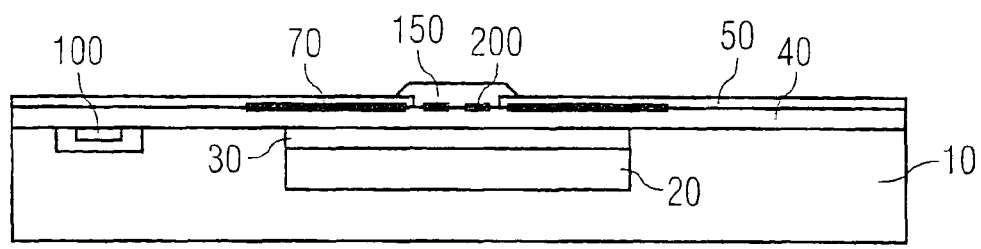
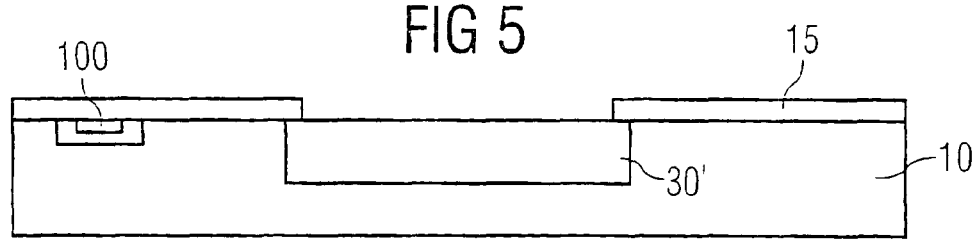

MICROMECHANICAL COMPONENT

This application is the national phase of PCT/DE02/02480 filed on Jul. 6, 2002.

FIELD OF THE INVENTION

The present invention is directed to a micromechanical component having a substrate and a cover layer deposited on the substrate, underneath the cover layer, a region of porous material being provided which mechanically supports and thermally insulates the cover layer.

BACKGROUND INFORMATION

Although applicable to any number of micromechanical components and structures, particularly sensors and actuators, the present invention, as well as its basic underlying problem definition are explained with reference to a micromechanical air-quality sensor which can be manufactured using the technology of silicon surface micromechanics.

Existing air-quality sensors are implemented using a gas-sensitive material on a ceramic material. The gas-sensitive material changes its resistance and/or its dielectric properties in dependence upon the concentration of the gas to be detected. To obtain a good sensitivity, it is necessary to heat the gas-sensitive material. This disadvantageously entails the use of a ceramic material and the associated large type of design with respect to the substantial heating power to be expended and the long response time.

The method of etching silicon to make it porous ("anodizing") constitutes related art, and it is described in numerous publications. The method of producing a cavity under a porous silicon layer is likewise already published (G. Lammel, P. Renaud, "Free-Standing Mobile 3D Microstructures of Porous Silicon", Proceedings of the 13$^{th}$ European Conference on Solid-State Transducers, Eurosensors XIII, The Hague, 1999, 535–536).

SUMMARY OF THE INVENTION

An advantage of the micromechanical component according to the present invention is that it renders possible a simple and cost-effective manufacturing of a component having a thermally decoupled, heatable cover-layer area, upon which a detector is provided.

For example, the use of porous silicon makes it relatively simple to produce a deep cavity having a superjacent cover layer. Moreover, it is possible to make a defined region on a wafer porous up to a defined thickness, and, optionally, to oxidize to a higher valency in order to create a stable framework having low thermal conductivity.

In the exemplary implementation of an air-quality sensor using this method, one obtains the following further advantages:

- low power consumption due to good thermal decoupling;
- integration of a sensor element on the chip;
- possible integration of a circuit on the sensor element;
- very small size, along with any desired geometry of the porous region;
- low response time because of the small mass that has to be retempered;
- capacitive or resistive evaluation possible;
- different materials are usable for the heating and/or measuring resistors or electrodes;
- a plurality of gas-sensitive materials may be employed on one chip.

An idea underlying the present invention is to provide, on the cover layer, a heating device to heat the cover layer above the region; and to provide, above the region, a detector to measure an electric property of a heated medium provided above the region on the cover layer.

In accordance with one preferred further refinement, the porous material is formed from the substrate material. This is readily possible, particularly in the case of a silicon substrate.

In accordance with another preferred refinement, a hollow space is formed underneath the region of porous material.

In accordance with yet another preferred refinement, the cover layer is formed by oxidizing the substrate surface and the surface of the porous region. This eliminates the need for depositing an additional cover layer.

In accordance with yet another preferred refinement, the region of porous material is completely oxidized. An oxidation of this kind is readily possible because of the porous structure, and it enhances the thermal insulating capability.

Yet another preferred refinement provides for the component to be an air-quality sensor, the medium being a gas-sensitive medium, and the detector having a capacitance detector and/or a resistance detector.

Still another preferred refinement provides for the detector to have printed conductors arranged on the cover layer.

Yet another preferred refinement provides for the detector to have printed conductors arranged on the insulation layer.

In yet another preferred refinement, the heating device extends at least partially underneath the medium.

BRIEF DESCRIPTION OF THE DRAWINGS

FIGS. 2–4 show manufacturing steps for manufacturing the air-quality sensor according to FIG. 1.

FIGS. 5–6 show manufacturing steps for manufacturing an air-quality sensor in accordance with a second specific embodiment of the present invention.

DETAILED DESCRIPTION

Figure 1:
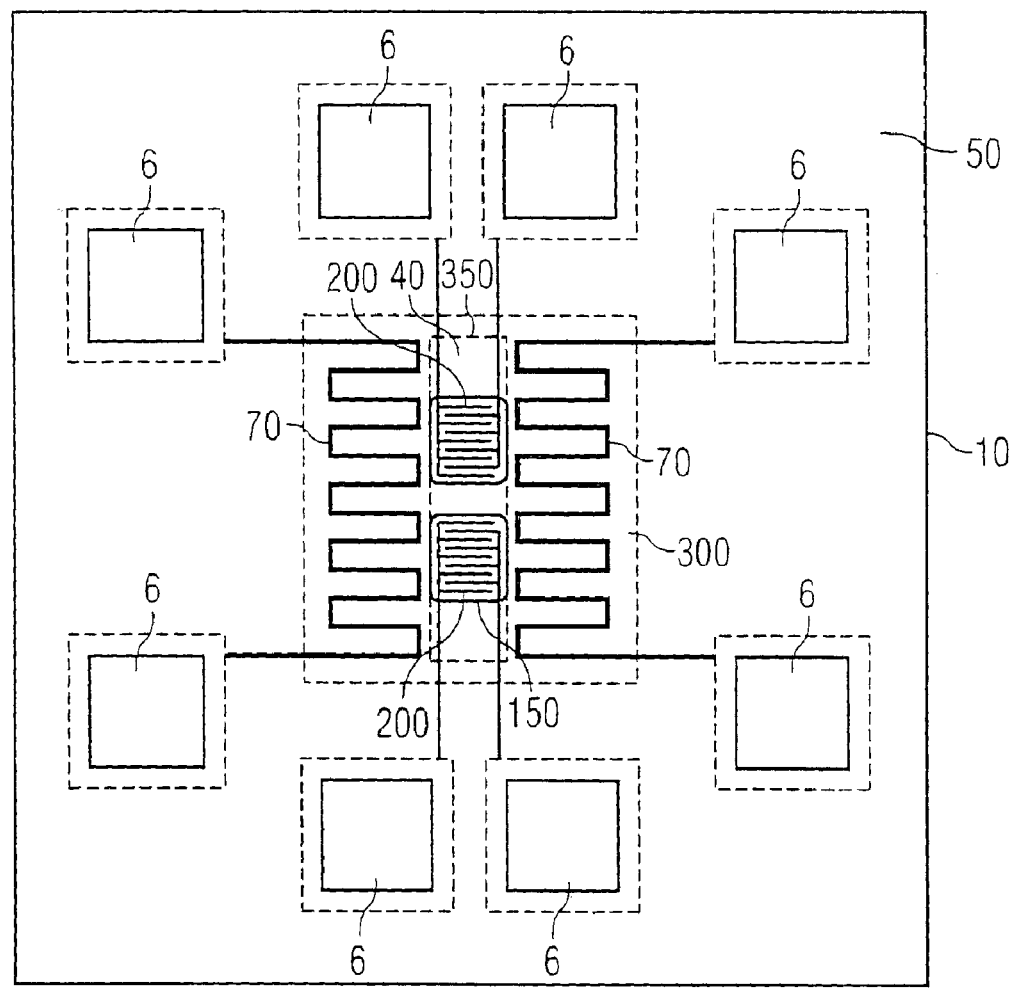
FIG. 1 shows a plan view of an air-quality sensor in accordance with a first specific embodiment of the present invention.

In the figures, components which are the same or functionally equivalent are denoted by the same reference numerals.

FIG. 1 is a plan view of an air-quality sensor in accordance with a first specific embodiment of the present invention.

In FIG. 1, reference numeral 6 denotes contact surfaces or contact pads; 10 a semiconductor substrate; 40 a cover layer situated on the surface of semiconductor substrate 10; and 300 the boundary of a region in which, underneath cover layer 40, a region 30 (compare, e.g., FIG. 3) of porous material is provided which mechanically supports and thermally insulates cover layer 40. In the present case, the substrate material is silicon and the porous material is anodized (porously etched) silicon.

In addition, reference numeral 50 denotes an insulation layer provided above cover layer 40; 70 a heating resistor between cover layer 40 and insulation layer 50; 350 the boundary of a region in which insulation layer 50 is removed from above cover layer 40; 200 an interdigital capacitor situated on cover layer 40; and 150 denotes a gas-sensitive material which covers the interdigital capacitors.

To operate the sensor structure shown in FIG. 1, gas-sensitive material 150 is heated by heating resistors 70, and the capacitance of interdigital capacitors 200 is measured in a generally known manner. The gas-sensitive material changes its dielectric properties in dependence upon the concentration of the gas to be detected. In this manner, the gas quality or concentration is able to be determined.

FIGS. 2–4 show manufacturing steps for manufacturing the air-quality sensor in accordance with FIG. 1.

In FIG. 2, in addition to the reference numerals already introduced, 15 denotes a mask, such as a resist mask, and 100 denotes circuit components of a sensor circuit that is not explained more closely. Substrate 10 shown in FIG. 2 is a silicon substrate.

According to FIG. 3, using the known method of porous etching, a structure is produced in which the substrate material is made porous in a certain region 30, and a hollow space 20 is subsequently formed underneath porous region 30. Thus a part of porous region 30 is removed, so the result is the structure shown in FIG. 3.

To produce the structure shown in FIG. 4, following removal of mask 15, porous region 30 is sealed by depositing cover layer 40, made, for example, of nitride, oxide, oxinitride, silicon carbide, or polysilicon. Another possibility for forming cover layer 40 provides for oxidizing the substrate surface and the surface of porous region 30.

It is not essential for this airtight sealing of hollow space 20 to follow the fabrication of hollow space 20, rather, it may also be accomplished as one of the last process steps. The latter has the advantage that, during processing, cover layer 40 does not bump out, which would lead to aberrations in a structuring process. The internal pressure that ultimately arises in hollow space 20 is dependent upon the pressure conditions prevailing during deposition or oxidation.

The measuring capacitors of interdigital capacitor 200, heating resistors 70, and optional measuring resistors (not shown) are then produced on cover layer 40. Further functional layers may be deposited and patterned between cover layer 40 and the printed conductors of heating resistors 70, i.e., above the printed conductors.

Above the measuring capacitors of interdigital capacitor 200, following application of insulation layer 50 which protects the formed structure from environmental influences, gas-sensitive material 150 is applied, which changes its dielectric properties as a function of the concentration of a gas to be recorded.

The specific embodiment at hand has a hollow space 20, having an enclosed vacuum underneath cover layer 40, and region 30, in order to ensure a good thermal insulation with respect to substrate 10 when gas-sensitive material 150 is heated by heating resistors 70.

Figure 6:
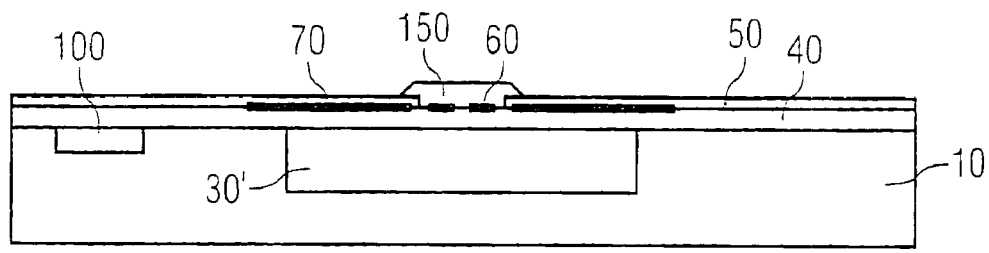

FIGS. 5–6 illustrate the manufacturing steps used to manufacture the air-quality sensor in accordance with a second specific embodiment of the present invention.

In the second specific embodiment shown with reference to FIGS. 5 and 6, no hollow space is formed underneath substrate region 30' that has been made porous. Rather, following removal of mask 15, porous region 30' is immediately sealed by deposition of cover layer 40 or by the oxidation.

In this context, the oxidation (not shown) has the advantage that the oxide has a lower thermal conductivity than the silicon, making it possible to ensure a better decoupling from substrate 10. As in the first specific embodiment, the printed conductors, etc., are produced on cover layer 40.

Figure 7:
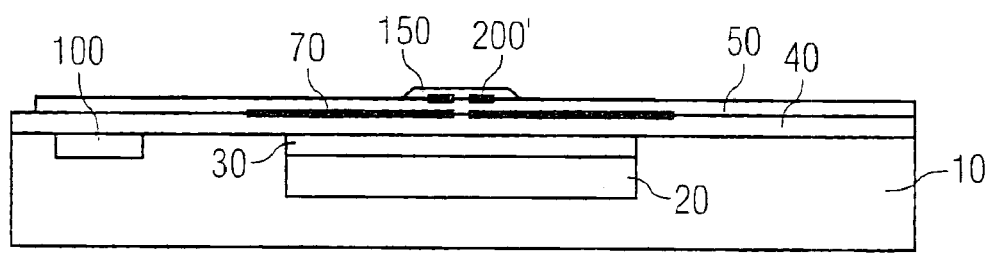
FIG. 7 shows a cross-sectional view of an air-quality sensor in accordance with a third specific embodiment of the present invention.

FIG. 7 is a cross-sectional view of an air-quality sensor in accordance with a third specific embodiment of the present invention.

In the third specific embodiment shown in FIG. 7, heating resistors 70 are provided on cover layer 40, and the measuring capacitors of interdigital capacitors 200' are provided on insulation layer 50, thus not directly on cover layer 40 as in the above exemplary embodiments. The advantage of this arrangement is that the heating structure may be placed directly underneath gas-sensitive material 150.

Figure 8:
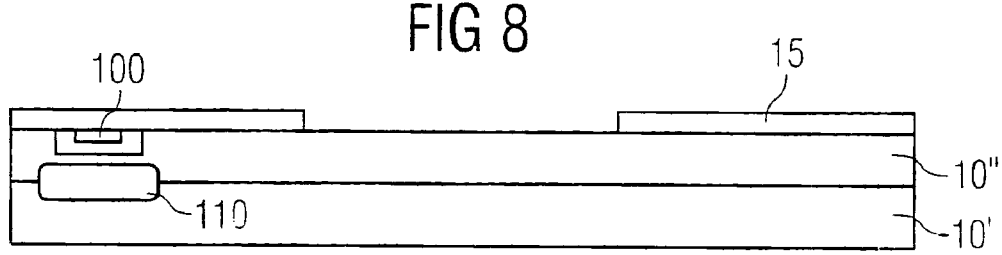
FIGS. 8–9 show manufacturing steps for manufacturing an air-quality sensor in accordance with a fourth specific embodiment of the present invention.
Figure 9:
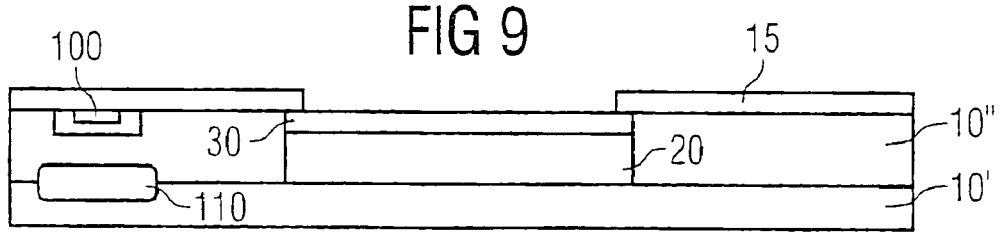

FIGS. 8–9 depict manufacturing steps for manufacturing an air-quality sensor in accordance with a fourth specific embodiment of the present invention.

In accordance with FIG. 8, a two-layer substrate 10', 10" is provided, in which an epitaxial layer 10" is provided on a wafer substrate 10'. Evaluation circuit 100 is additionally insulated by a buried region 110. The benefit of such a design is that the formation of porous region 30, 30' on bottom wafer substrate 10' may be stopped by properly doping components 10', 10".

Although the present invention is described above on the basis of preferred exemplary embodiments, it is not limited to them, and may be modified in numerous ways.

In the above examples, the air-quality sensor according to the present invention has been presented in simple forms in order to elucidate its basic principles. Combinations of the examples and substantially more complicated refinements using the same basic principles are, of course, conceivable.

For example, instead of changing the dielectric properties, it is also possible to change the electric resistance of the medium, e.g., of the gas-sensitive medium, using appropriate measuring electrodes.

In addition, it is possible to selectively etch porous region 30, 30' subsequently to or in-between the above process steps. For this purpose, one or a plurality of openings may be produced in cover layer 40, through which a selectively acting etching medium, in a fluid or gaseous state, is able to partially or completely dissolve out the porous region. The openings may subsequently be sealed again, a vacuum being preferably enclosed in hollow space 20 in the process in order to ensure an optimal thermal decoupling between cover layer 40 and substrate 10. The openings may likewise be deliberately not closed. In this manner, the middle cover layer region having functional elements may be formed in such a way that it is only still joined by a few land features (resist lines) to the substrate outside of the cavity (e.g., connection by only two land features in the form of a bridge).

Also possible is the additional integration of a temperature sensor on the cover layer outside of the porous region in order to precisely set or regulate the desired temperature.

It is also possible to provide different media on the cover layer or the insulation layer above the porous region which are sensitive to various gases. This makes it possible to measure a plurality of gases using the same sensor element.

In addition, it is possible to realize the porous region so that it continues right through to the bottom side of the substrate.

Finally, any micromechanical base materials may be used, and not only the silicon substrate cited exemplarily.

In addition, the electric leads (not shown in FIG. 7) to the interdigital structures may be situated underneath an electrically insulating protective layer. Also, the electrical connection by contact vias (openings) in the insulation layer may be implemented by electrical leads which are situated in the same plane as heating resistors 70.

| | |
|---|---|
| 10; 10', 10" | Si substrate |
| 6 | contact pads |
| 40 | cover layer |
| 300 | boundary of porous region under 40 |
| 350 | boundary region without insulation layer |
| 70 | heating resistor |
| 200, 200' | interdigital capacitor |
| 150 | gas-sensitive medium |
| 15 | mask |
| 100 | evaluation circuit |
| 110 | buried layer |
| 20 | hollow space |
| 30, 30' | porous region |
| 50 | insulation layer |

What is claimed is:

1. A micromechanical component comprising:
   a substrate;
   a cover layer deposited on the substrate;
   a region of porous material situated underneath the cover layer, the region mechanically supporting and thermally insulating the cover layer;
   a heating device situated on the cover layer for heating the cover layer above the region;
   a detector situated above the region for measuring an electric property of a heated medium provided above the region on the cover layer; and
   a structure including a hollow space underneath the region.

2. The micromechanical component according to claim 1, wherein the porous material of the region is formed from a material of the substrate.

3. The micromechanical component according to claim 1, wherein the cover layer is formed by oxidizing a surface of the substrate and a surface of the region of porous material.

4. The micromechanical component according to claim 1, wherein the region of porous material is completely oxidized.

5. A micromechanical component comprising:
   a substrate;
   a cover layer deposited on the substrate;
   a region of porous material situated underneath the cover layer, the region mechanically supporting and thermally insulating the cover layer;
   a heating device situated on the cover layer for heating the cover layer above the region; and
   a detector situated above the region for measuring an electric property of a heated medium provided above the region on the cover layer, wherein the component is an air-quality sensor, the medium is a gas-sensitive medium, and the detector includes at least one of a capacitance detector and a resistance detector.

6. The micromechanical component according to claim 1, wherein the detector includes printed conductors situated on the cover layer.

7. The micromechanical component according to claim 1, further comprising an insulation layer, and wherein the detector includes printed conductors situated on the insulation layer.

8. The micromechanical component according to claim 1, wherein the heating device extends at least partially underneath the medium.

9. The micromechanical component according to claim 1, wherein the component is an air-quality sensor, the medium is a gas-sensitive medium, and the detector includes at least one of a capacitance detector and a resistance detector.

10. The micromechanical component according to claim 5, wherein the porous material of the region is formed from a material of the substrate.

11. The micromechanical component according to claim 5, further comprising:
    a structure including a hollow space underneath the region.

12. The micromechanical component according to claim 5, wherein the cover layer is formed by oxidizing a surface of the substrate and a surface of the region of porous material.

13. The micromechanical component according to claim 5, wherein the region of porous material is completely oxidized.

14. The micromechanical component according to claim 5, wherein the detector includes printed conductors situated on the cover layer.

15. The micromechanical component according to claim 5, further comprising an insulation layer, and wherein the detector includes printed conductors situated on the insulation layer.

16. The micromechanical component according to claim 5, wherein the heating device extends at least partially underneath the medium.

* * * * *

UNITED STATES PATENT AND TRADEMARK OFFICE
CERTIFICATE OF CORRECTION

PATENT NO. : 6,906,392 B2
DATED : June 14, 2005
INVENTOR(S) : Hubert Benzel et al.

It is certified that error appears in the above-identified patent and that said Letters Patent is hereby corrected as shown below:

<u>Title page,</u>
Item [73], Assignee, change "paragon" to -- paragon AG --.
Item [30], Foreign Application Priority Data, change
"July 6, 2002 (DE) ……………….. PCT/DE02/02480" to
-- July 25, 2001 (DE) ……………….. 101 36 164.5 --.

Signed and Sealed this

Third Day of January, 2006

JON W. DUDAS
*Director of the United States Patent and Trademark Office*